United States Patent
Ohmer

(10) Patent No.: US 11,090,187 B2
(45) Date of Patent: Aug. 17, 2021

(54) HOT WATER BOTTLE CONTAINING PHASE CHANGE MATERIAL

(71) Applicant: WFI WÄRMFLASCHENINNOVATION UG (HAFTUNGSBESCHRÄNKT), Gröbenzell (DE)

(72) Inventor: Benjamin Ohmer, Gröbenzell (DE)

(73) Assignee: WFI WÄRMFLASCHENINNOVATION UG (HAFTUNGSBESCHRÄNKT), Munich (DE)

( * ) Notice: Subject to any disclaimer, the term of this patent is extended or adjusted under 35 U.S.C. 154(b) by 320 days.

(21) Appl. No.: 15/113,951

(22) PCT Filed: Jan. 23, 2015

(86) PCT No.: PCT/EP2015/051342
§ 371 (c)(1),
(2) Date: Jul. 25, 2016

(87) PCT Pub. No.: WO2015/110574
PCT Pub. Date: Jul. 30, 2015

(65) Prior Publication Data
US 2016/0346116 A1 Dec. 1, 2016

(30) Foreign Application Priority Data

Jan. 23, 2014 (DE) .................... 10 2014 000 941.6
Jan. 26, 2014 (DE) .................... 10 2014 000 799.5
(Continued)

(51) Int. Cl.
*A61F 7/08* (2006.01)
*A61F 7/00* (2006.01)
*A61F 7/02* (2006.01)

(52) U.S. Cl.
CPC ............... *A61F 7/08* (2013.01); *A61F 7/086* (2013.01); *A61F 2007/0098* (2013.01); *A61F 2007/0279* (2013.01); *A61F 2007/0293* (2013.01)

(58) Field of Classification Search
CPC .......... A61F 7/08; A61F 7/0085; A61F 7/103; A61F 2007/0292; A61F 2007/0098;
(Continued)

(56) References Cited

U.S. PATENT DOCUMENTS 4,169,493 A * 10/1979 Segalowicz ............. B29C 49/76
383/96
4,580,547 A * 4/1986 Kapralis .................... A61F 7/03
126/263.03
(Continued)

FOREIGN PATENT DOCUMENTS

CN 102105119 A 6/2011
CN 202776703 U 3/2013
(Continued)

OTHER PUBLICATIONS

Xavier Py, Régis Olives, Sylvain Mauran, Paraffin/porous-graphite-matrix composite as a high and constant power thermal storage material, International Journal of Heat and Mass Transfer, vol. 44, Issue 14, 2001, p. 2727-2737.*
(Continued)

*Primary Examiner* — Eun Hwa Kim
*Assistant Examiner* — Adam Z Minchella
(74) *Attorney, Agent, or Firm* — J-TEK Law PLLC; Jeffrey D. Tekanic; Scott T. Wakeman

(57) ABSTRACT

A heating device has a receiving space for holding water and a flexible wall. An inorganic phase change material for at least temporarily controlling a temperature of the water is disposed in the receiving space. The phase change material
(Continued)

has a property of absorbing energy during an endothermic phase transition when warmed by the water and releasing energy in the form of heat during an exothermic phase transition. The phase change material may partially or completely undergo the endothermic phase transition when hot water is poured into the receiving space. The phase change material is disposed in a housing formed as a flexible film composed of a polymer material. An actuating means for triggering the exothermic phase transition is in fluid communication with the phase change material.

21 Claims, 11 Drawing Sheets

(30) Foreign Application Priority Data

Apr. 9, 2014 (DE) .................... 10 2014 005 167.6
May 21, 2014 (DE) .................... 10 2014 007 514.1

(58) Field of Classification Search
CPC ...... A61F 2007/0054; A61F 2007/0092; A61F 2007/0203; A61F 2007/0277; A61F 2007/108; A61F 2007/0085; A61F 7/086; A61F 2007/0279; A61F 2007/0293; B29D 22/006
See application file for complete search history.

(56) References Cited

U.S. PATENT DOCUMENTS

| | | | |
|---|---|---|---|
| 5,069,208 A | 12/1991 | Noppel et al. | |
| 5,603,729 A * | 2/1997 | Brown | A61F 7/03 607/114 |
| 6,083,256 A * | 7/2000 | Der Ovanesian | F28D 20/02 607/114 |
| 6,302,902 B1 * | 10/2001 | Benja-Athon | A61F 7/02 607/104 |
| 2004/0186541 A1 * | 9/2004 | Agarwal | A61P 43/00 607/114 |
| 2005/0021115 A1 | 1/2005 | Yue | |
| 2008/0119916 A1 * | 5/2008 | Choucair | A61F 7/10 607/104 |
| 2008/0255644 A1 | 10/2008 | Carson | |
| 2009/0229593 A1 * | 9/2009 | Komiya | A61F 7/02 126/263.01 |
| 2010/0010599 A1 * | 1/2010 | Chen | A61F 7/02 607/112 |
| 2011/0204065 A1 * | 8/2011 | Kolowich | A47G 19/127 220/592.16 |
| 2012/0305231 A1 | 12/2012 | Liang et al. | |
| 2012/0330388 A1 | 12/2012 | Chen et al. | |
| 2014/0261380 A1 * | 9/2014 | Rademacher | A61F 7/0097 126/263.01 |

FOREIGN PATENT DOCUMENTS

| | | |
|---|---|---|
| CN | 103340712 A | 10/2013 |
| DE | 2906299 A1 | 8/1980 |
| DE | 202007003922 U1 | 7/2007 |
| GB | 2436801 A | 10/2007 |
| JP | S5324188 U | 3/1978 |
| JP | S6171111 U | 5/1986 |
| JP | H01312356 A | 12/1989 |
| JP | H063569 Y2 | 2/1994 |
| JP | 3141182 U | 3/2001 |
| JP | 3163042 U | 9/2010 |
| JP | 2011139757 A | 7/2011 |
| WO | 0121117 A1 | 3/2001 |
| WO | WO2007117159 A1 | 10/2007 |
| WO | WO2009139877 A1 | 11/2009 |

OTHER PUBLICATIONS

Xavier Py, Regis Olives, Sylvain Mauran, Paraffin/porous-graphite-matrix composite as a high and constant power thermal storage material, International Journal of Heat and Mass Transfer, vol. 44, Issue 14, 2001, p. 2727-2737 (Year: 2001).*
Office Action from the Japanese Patent Office dated Sep. 18, 2018 in counterpart Japanese application No. 2016-539253, and translation thereof.
Office Action from the German Patent Office dispatched Jun. 6, 2014 in related German application No. 10 2014 000 941.6, and translation thereof.
Search report from Chinese Patent Office in related Chinese application No. 2015800031144 dated Apr. 18, 2018 and translation of substantive portions thereof.
Anonymous: "Sodium acetate—Wikipedia", Dec. 29, 2013 (Dec. 29, 2013), XP055721869, Found on the Internet: URL:https://en.wikipedia.org.
Communication from the European Patent Office in counterpart EP application No. 15 703 482.8 dated Aug. 18, 2020, with machine translation thereof.

* cited by examiner

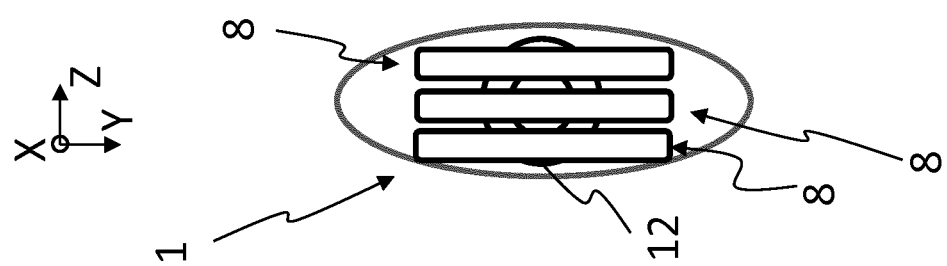
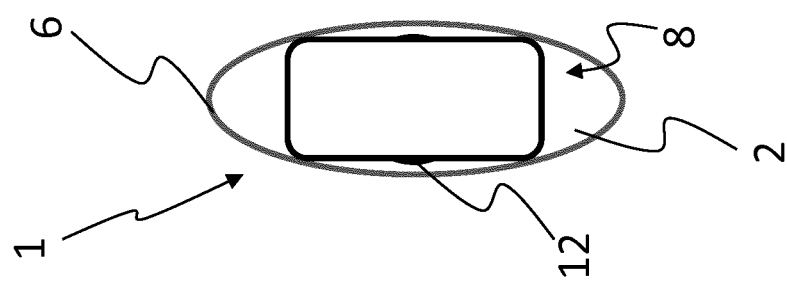
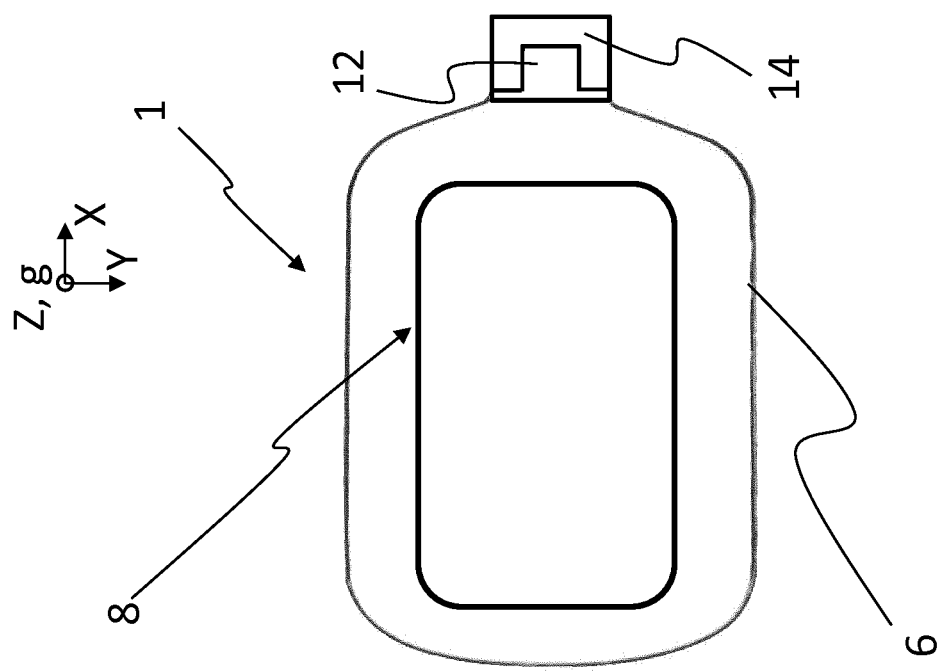
Fig. 2c
Fig. 2b
Fig. 2a

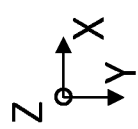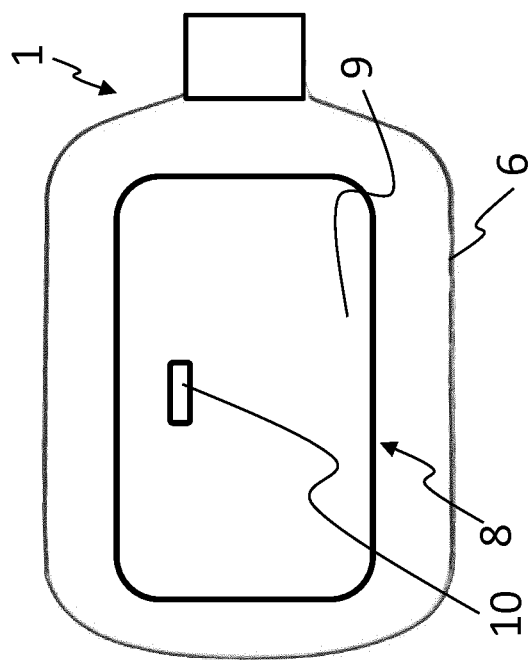
Fig. 6

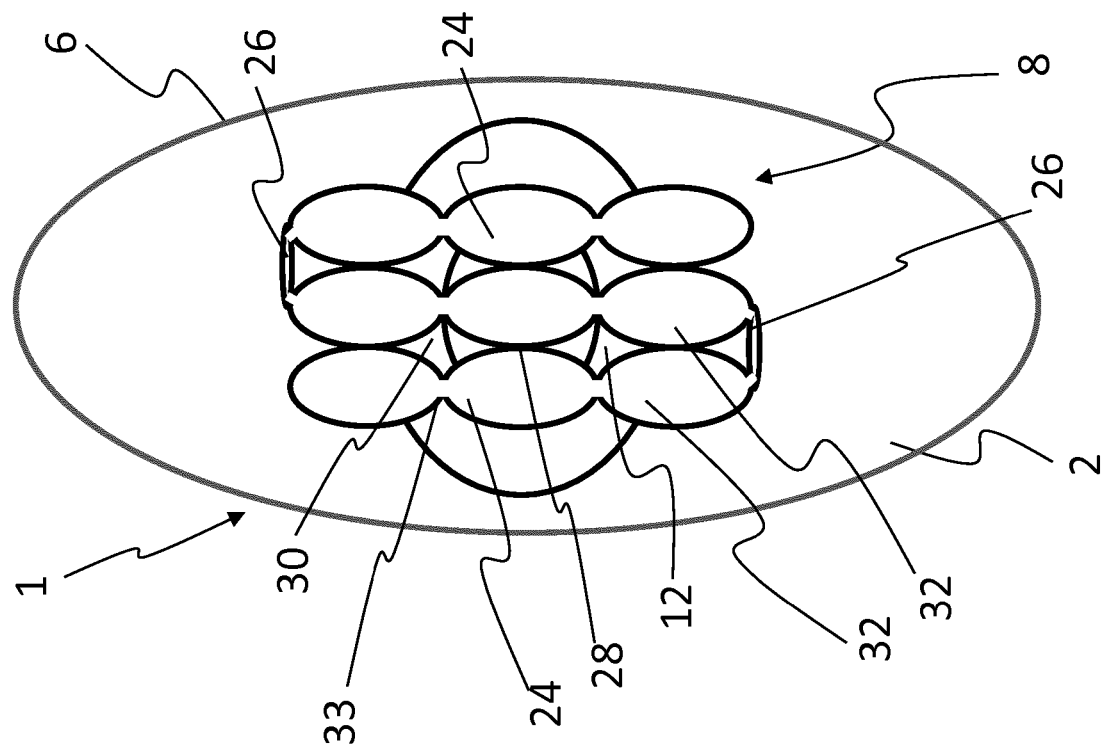
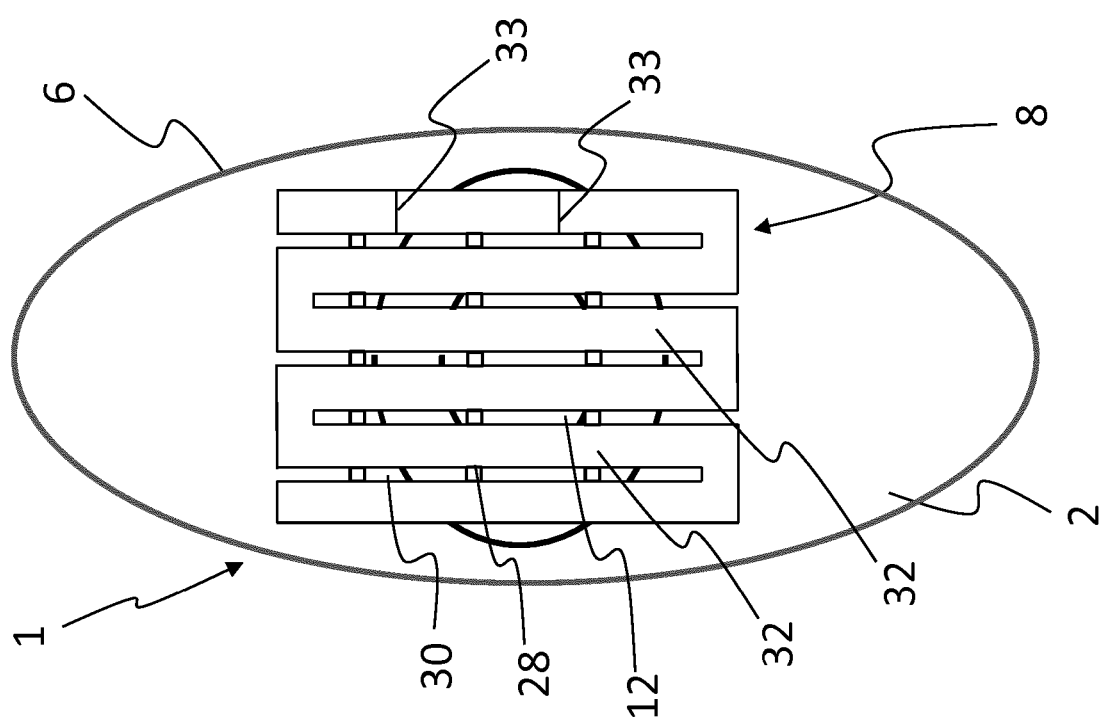

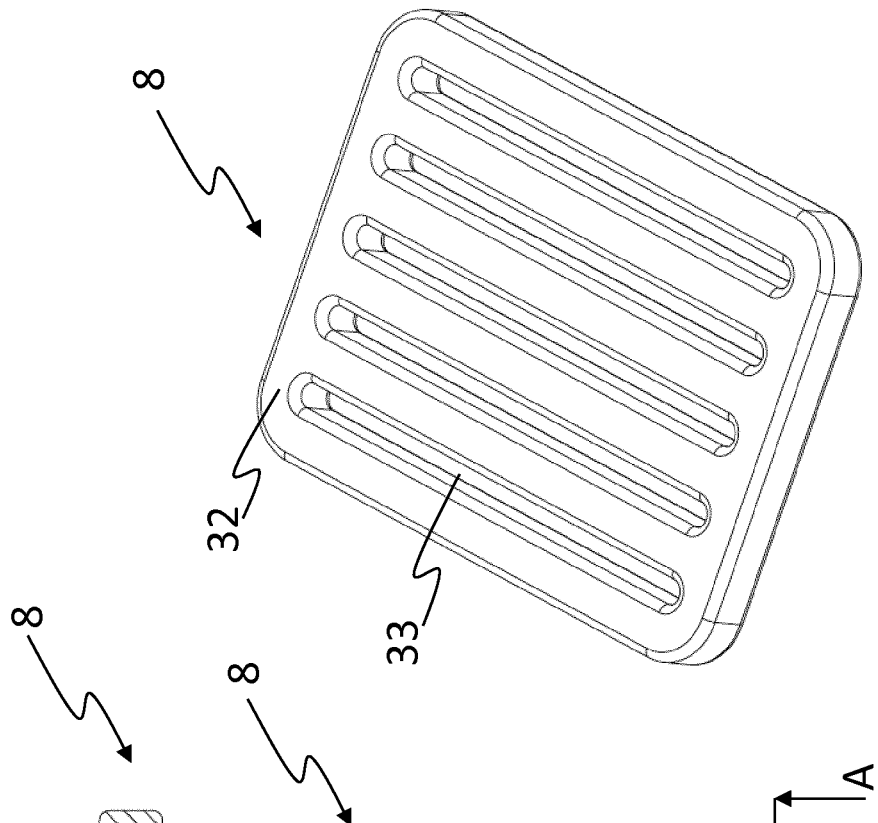
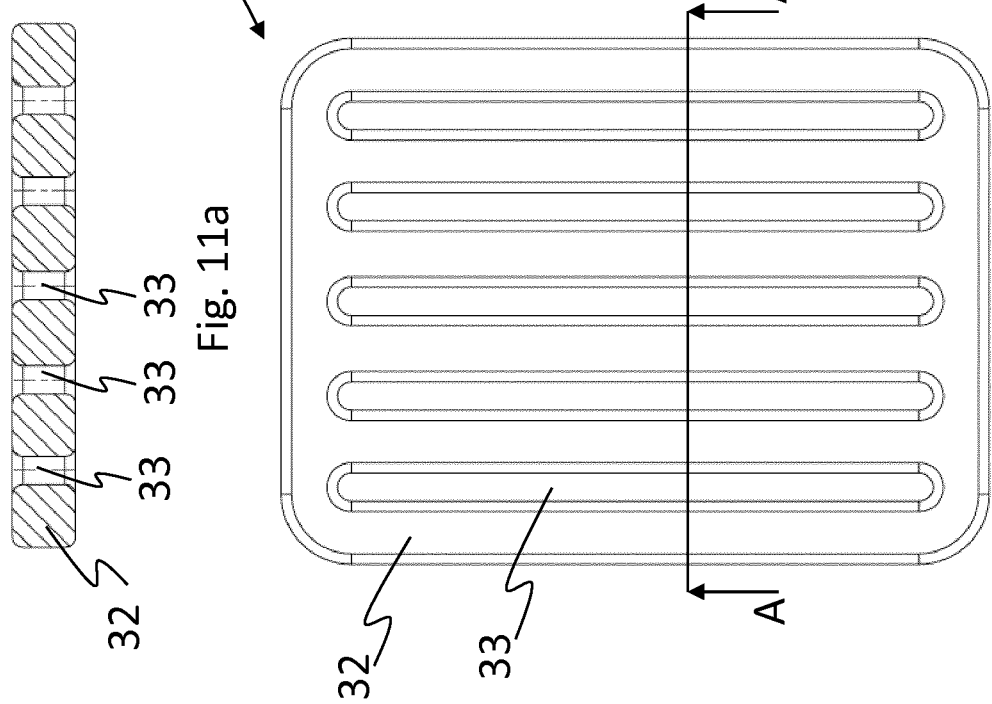
Fig. 11a
Fig. 11b
Fig. 11c

HOT WATER BOTTLE CONTAINING PHASE CHANGE MATERIAL

CROSS-REFERENCE

This application is the US national stage of International Patent Application No. PCT/EP2015/051342 filed on Jan. 23, 2015, which claims priority to German Patent Application No. 10 2014 007 514.1 filed on May 21, 2014, German Patent Application No. 10 2014 005 167.6 filed on Apr. 9, 2014, German Patent Application No. 10 2014 000 799.5 filed on Jan. 29, 2014 and German Patent Application No. 10 2014 000 941.6 filed on Jan. 23, 2014.

TECHNICAL FIELD

The present invention generally relates to a heating device, such as a hot water bottle or a heating pad.

RELATED ART

Heating devices, such as hot water bottles and grain pillows, have been around for many years. These types of heating devices however all have the same problem in that they can be filled by users with water that is too hot or are heated up too much by a heating device, such as an oven. The extreme heat can result in burns to the skin. To avoid burns, the "Hot Water Bottles Safety Standard BS 1970" was introduced, which was replaced by the "Hot Water Bottles Safety Standard BS 1970:2012" in 2012. According to this standard, hot water bottles must be manufactured with a certain wall thickness, to limit the heat transfer. Furthermore, according to this standard, hot water bottles must have a warning label attached to them stating that they cannot be filled with boiling water.

Attempts to solve this problem has been made in several patent and utility model publications. For example, German utility model no. DE 77 07 739 discloses different configuration of the walls of the hot water bottle, which cause varying degrees of heat to be transferred. German utility model no. 85 04 306 U1 discloses a hot water bottle, which has an insulating layer on one side. German patent no. DE 691 01 711 T2 discloses a hot water bottle, wherein the two sides of the hot water bottle have different flocking.

All previous approaches have not been very successful as many users still use a kettle to heat the water for the hot water bottle. As kettles generally only turn off when the water is boiling, most people use this boiling water to fill the hot water bottle, which is why it can be dangerously hot.

Many users also use very hot water because they hope to keep the hot water bottle warmer for longer with hotter water. This practice reveals another problem relating to known hot water bottles. Current hot water bottles have a substantially continuous cooling rate, which means that the hot water bottle is either too hot or too cold for most of the time it is being used.

SUMMARY

It is one non-limiting object of the present teachings to disclose a heating device that overcomes one or more of the aforementioned problems and that also provides longer-lasting comfort during usage of the heating device.

According to one aspect of the present teachings, a heating device, e.g., a hot water bottle or a heating pad, can be brought into direct or indirect contact with a living being, e.g., a person and/or an animal. Such a heating device preferably comprises at least one receiving space for holding a flowable material, wherein the receiving space is at least formed by a flexible wall that can be brought into at least indirect contact with the living being. Furthermore, at least one or exactly one latent heat storage material is provided or the heating device comprises at least one or exactly one latent heat storage means, wherein the latent heat storage means is arranged in such a manner to ensure that, at least for some of the time, it performs a temperature control (cooling or heating) of the flowable material, wherein the latent heat storage means includes a phase change material, e.g., sodium acetate, and the phase change material absorbs energy during an endothermic phase transition brought about by warming and releases energy during an exothermic phase transition in the form of heat.

Such an embodiment is beneficial because, on the one hand, excess heat is initially removed from the flowable material for later use, thereby reducing the risk of burns and, on the other hand, the later release of stored heat provides longer-lasting comfort. The phase change material causes the flowable material to cool as a result of a partial or complete endothermic phase transition, thereby allowing the heat stored in the phase change material to be released at a later time in a preferably constant or substantially constant manner to the flowable material and/or to the wall. It has been demonstrated in experiments that heating devices according to the present teachings provide not only significantly more homogeneous heat, but also that the duration of the heat, particularly in an optimal heat range between 38° C. and 48° C., is longer. Therefore, heating devices according to the present teachings, when compared to an identical heating device, e.g., a hot water bottle without a latent heat storage means, remain warmer for a longer time period under the same circumstances, e.g., the temperature of the flowable material, the amount of the flowable material and the ambient temperature, and particularly remain warmer for longer in an optimal temperature range. This phenomenon is explained by a strong reduction in the heat dissipation to the surroundings in the first few minutes owing to the heat absorption by the latent heat storage means. The higher the temperature difference between the surroundings and the heating device, the greater the heat dissipation to the surroundings in the absence of the latent heat storage means. As there is a substantial cooling of the flowable material at first due to a portion of the heat from the flowable material being transferred to the latent heat storage means, heating devices according to the present teachings cause the heat dissipation to the surroundings to be reduced while the flowable material is extremely hot, and storage of the excess heat of the flowable material in the latent heat storage means allows the heat to be released to the surroundings over a longer period.

The temperature control of the flowable material can mean a cooling of the flowable material or can take place during the cooling of the flowable material, whereby the temperature control of the flowable material or flowable substance, which can be a mixture of materials or substances, preferably means the supply of heat to the flowable material, wherein the heat preferably causes the heating of the flowable material, the maintenance of the temperature of the flowable material or the reduction in the cooling speed of the flowable material.

In other words, the latent heat storage means preferably comprises a phase change material, e.g., sodium acetate, wherein the phase change material first absorbs energy in a first phase transition (e.g., liquification) as a result of heating and then releases energy in the form of heat during a second phase transition (e.g., solidification). Phase change materials preferably contain sodium acetate trihydrate or sodium acetate or paraffins or a mixture of these materials. Sodium acetate trihydrate has a melting temperature of substantially or exactly 58° C. while, paraffin, e.g., paraffin wax, has a melting temperature of approx. or exactly 60° C. The phase change material preferably has a melting temperature of higher than 36° C., e.g., of higher than 40° C., e.g., of higher than 42° C., e.g., of higher than 45° C., e.g., of higher than 47° C., e.g., of higher than 50° C., e.g., of higher than 52° C., e.g., of higher than 55° C., e.g., of higher than 56° C., going up to, for example 60° C. or up to 65° C. or up to 70° C. or up to 80° C. Thus, according to the present teachings, a phase change material is preferably used that has a melting temperature of between 30° C. and 80° C. and preferably between 36° C. and 70° C. and more preferably between 40° C. and 65° C., e.g., between 45° C. and 63° C. The phase change material preferably comprises salt constituents and e.g., preferably comprises one or more salts in predominant mass proportions.

According to another preferred embodiment of the present teachings, the latent heat storage means is configured in such a way that, for a defined amount of a defined temperature controlled flowable material, the phase change material completely undergoes an endothermic phase transition, whereby the cooling rate of the flowable material is also preferably defined. The benefit of this embodiment is that a stable state is reached through the complete phase transition, in which the absorbed heat is stored and always available.

According to another preferred embodiment of the present teachings, the latent heat storage means comprises an actuating means, e.g., a clicker comprising at least one metal to trigger the exothermic phase transition.

If, for example, the temperature of the flowable material falls below the temperature resulting during the phase transition or the exothermic phase transition, e.g., to room temperature, the actuating means can trigger the phase transition of the phase change material which leads to a warming up of the flowable material.

The actuating means is preferably partially or completely surrounded by the phase change material and is preferably in direct contact with it.

According to another preferred embodiment of the present teachings, the latent heat storage means is preferably configured in such a way that, for a defined amount of a defined temperature controlled flowable material, the phase change material partially undergoes an endothermic phase transition, whereby the cooling rate of the flowable material is also preferably defined.

For an amount A of flowable material, e.g., water, a temperature T of the flowable material and a cooling rate of R of the flowable material, the latent heat storage means thus preferably takes on a three-dimensional outer shape and thus preferably has a defined amount of phase change material arranged therein, wherein the amount of phase change material is chosen depending on the three-dimensional outer shape of the latent heat storage means, so that the phase change material only partially undergoes the endothermic phase transition. Preference here is given to the rule that, for the same amount A of flowable material, the same temperature T and the same cooling rate of R, increasing the surface area of the three-dimensional outer shape of the latent heat storage means leads to an increase in the amount of phase change material.

When the flowable material cools off and falls e.g., below the temperature at which the phase change material changes its phase or state, that phase change material releases heat and thus reverses the partial endothermic phase transition. The phase change material releases the previously absorbed energy during the reversal, preferably substantially or completely in the form of heat, to the flowable material.

Phase change material that has not completely changed the phase helps to reverse the partially completed phase change, whereby the phase change material gives off heat. On the other hand, phase change material that has completely changed the phase only changes the phase or the state reached after a triggering effect that can be created or initiated by the actuating means. This embodiment thus provides a kind of thermal buffer benefit.

In the case of a heating device that is being filled with temperature controlled (heated) flowable material, such as, for example, in the case of a hot water bottle, the phase change material first absorbs the heat from the flowable material, thereby cooling down the flowable material. It is noted that injuries or burns of the skin are more likely to occur when the temperature of the heated flowable material is not brought to an ideal temperature (e.g. 50°–60° C.) prior to usage of the heating device, i.e. burns result when the flowable material is much hotter (e.g. 95° C.). By cooling down the temperature of the flowable material using the phase change material, excess heat from the flowable material is efficiently stored in the phase change material. The stored heat is then released by the phase change material as soon as the temperature of the flowable material drops below a threshold temperature. The heat released by the phase change material then preferably causes the temperature of the flowable material to be constant or substantially constant in the range of the threshold temperature or the heat released by the phase change material causes, at the very least, a slower cooling off of the flowable material.

According to another preferred embodiment of the present teachings, the receiving space has a closable filling/emptying opening for supplying the e.g., heated flowable material into the receiving space and for pouring the cooled flowable material out of the receiving space.

This embodiment has the benefit that the flowable material can be heated or temperature controlled outside the heating device.

According to another preferred embodiment of the present teachings, the receiving space is encapsulated in such a manner that the flowable material remains permanently in the receiving space. This in effect means particular preferably that the flowable material can only be removed from the receiving space if the receiving space is damaged or destroyed. There is, e.g., no filling and/or emptying opening in this embodiment of the present teachings. This embodiment has the benefit that the latent heat storage means and the flowable material can be heated at the same time by the same heat source, such as an oven, a microwave oven, a pan, etc. This avoids having to do time consuming exchange activities and, since there is no closure device, there is no risk of it being closed incorrectly, making the use of the heating device safer.

According to another preferred embodiment of the present teachings, the at least or exactly one latent heat storage means is/are placed inside the receiving space or on the wall of the receiving space or form part of the wall.

Having the latent heat storage means in the area of the wall or on the wall is preferred, particularly if in the receiving space or outside of the receiving space.

According to another preferred embodiment of the present teachings, the ratio between the amount or mass of flowable material that can be held in the receiving space and the amount or mass of the phase change material lies between 2:1 and 7:1, preferably between 2.5:1 and 5.5:1 and best between 2.5:1 and 4.5:1. Thus, preferably the ratio between the amount of flowable material that can be held in the receiving space and the amount of the phase change material lies between 2:1 and 6:1, preferably between 2.5:1 and 5.5:1 and best between 2.5:1 and 4.5:1 or the ratio between the mass of flowable material that can be held in the receiving space and the mass of phase change material lies between 2:1 and 6:1, preferably between 2.5:1 and 5.5:1 and best between 2.5:1 and 4.5:1. For the purposes of the present teachings, the ratio between the amount or mass of flowable material that can be held in the receiving space and the amount or mass of the phase change material can lie between 2.5:1 and 4:1, but lies preferably between 2.5:1 and 3.5:1 and best between 2:1 and 4:1.

According to another preferred embodiment of the present teachings, the walls of the heating device may have different insulating capacities. The wall that will be in contact with the body of a living being is preferably less insulated than the wall in the receiving space that is spaced apart therefrom. This embodiment has the benefit that the heat, which is released to the surroundings, is reduced and thus leads to an extension of the duration during which heat is released to the living being and during which heat of the latent heat storage can be absorbed by the flowable material.

The present teachings also relate to a heating device, e.g., a hot water bottle or a heating pad, which is to be brought into indirect contact with a living being, which preferably comprises at least a receiving space to hold a flowable material, wherein the receiving space is separated at least by a partially flexible wall, wherein the flexible wall is designed to come into at least indirect contact with a living being, and which has been equipped with a latent heat storage means, wherein the latent heat storage means is arranged so that the latent heat storage means can at least temporarily control the temperature of the flowable material and wherein the latent heat storage means is designed as a thermochemical heat accumulator.

The present teachings further relate to a manufacturing method for the heating device, e.g., a hot water bottle or a heating pad, for, at the very least, indirect contacting with a living being. The manufacturing method preferably includes at least the steps of providing two blank plates, which together form the walls of the hot water bottle, arranging at least one latent heat storage means between the blank plates, wherein the latent heat storage means comprises a phase change material, wherein the phase change material absorbs energy during an endothermic phase transition and releases energy in the form of heat during an exothermic phase transition, and joining the blank plates to each other, e.g., by means of vulcanisation. It is also, however, conceivable that the manufacturing process preferably comprises at least the steps of inserting a thermoplastic blank in a blow mould, forming of the hot water bottle by introducing air into the blank, inserting a latent heat storage means into the interior of the produced form through an opening of the hot water bottle, wherein the latent heat storage means comprises a phase change material, wherein the phase change material absorbs energy during an endothermic phase transition and releases energy in the form of heat during an exothermic phase transition, inserting a threaded inlet and outlet means into the opening of the hot water bottle and connecting the inlet and outlet means to the hot water bottle.

This manufacturing method has the benefit that it provides for the manufacture of a hot water bottle with an integrated latent heat storage means.

Furthermore, the present teachings relate to a latent heat storage means for use as a retrofit element for hot water bottles or a hot water bottle latent heat storage means for insertion into an existing hot water bottle at least partially and preferably mainly made of rubber or plastic, e.g., PVC, existing hot water bottle, whereby the hot water bottle has an opening with an opening diameter of less than or equal to 30 mm, e.g., smaller or equal to 29 mm, e.g., smaller or equal to 28 mm, e.g., smaller or equal to 27 mm, e.g., smaller or equal to 26 mm, e.g., smaller or equal to 25 mm, and which holds at least 0.4 litres of flowable material, e.g., water, e.g., at least 0.5 litres, e.g., at least 0.75 litres, e.g., at least 1 litre, e.g., at least 1.2 litres, e.g., at least 1.5 litres, e.g., at least 1.75 litres, e.g., at least 2 litres, and has a wall thickness of at least 1 mm, e.g., of at least 1.1 mm, e.g., of at least 1.2 mm, e.g., of at least 1.3 mm, e.g., of at least 1.4 mm, e.g., of at least 1.5 mm. The hot water bottle latent heat storage means has at least one wall that forms or defines an outer three-dimensional shape of the hot water bottle latent heat storage means, with the wall acting as a boundary for a retention space in which a phase change material is located, wherein the phase change material absorbs energy during an endothermic phase transition and releases energy in the form of heat during an exothermic phase transition, wherein the phase change material has a melting temperature of more than 36° C., e.g., of more than 40° C., e.g., of more than 42° C., e.g., of more than 45° C., e.g., of more than 47° C., e.g., of more than 50° C., e.g., of more than 52° C., e.g., of more than 55° C., e.g., of more than 56° C., for example up to 60° C. or up to 65° C. or up to 70° C., and which is provided in a quantity or mass which allows the phase change material, with the hot water bottle preferably at ⅔rds full, and e.g., when completely full, with phase change material heated above a melting temperature, e.g., of 80° C., e.g., of 95° C. heated flowable material, e.g., water, at an ambient temperature of 20° C. or of 30° C. or of 36° C. or of 40° C. to only partially undergo an endothermic phase transition. The hot water bottle is preferably made from a polymer or elastomer material, e.g., rubber, PVC or latex. It is preferable if the exothermic phase transition happens immediately or for the most part immediately after the endothermic phase transition.

The hot water bottle latent heat storage means or the latent heat storage means preferably includes a film-like housing or sleeve, i.e. the wall of the hot water bottle latent heat storage means is preferably flexible. The wall or housing of the latent heat storage means or the hot water bottle latent heat storage means particularly preferably consists of a polymer material, e.g., a waterproof, e.g., at least at ambient pressure, and temperature stable polymeric material up to at least 100° C., preferably or substantially up to 110° C., preferably or substantially up to 120° C., preferably or substantially up to 130° C., preferably or substantially up to 140° C., preferably or substantially up to 150° C., preferably or substantially up to 160° C., preferably or substantially up to 170° C., preferably or substantially up to 200° C., preferably or substantially up to 250° C., preferably or substantially up to 300° C., preferably or substantially up to 350° C.

The hot water bottle latent heat storage means can also be formed from a plurality of individual, physically separate or interconnected receiving spaces, each filled with a phase change material and preferably in a film-like housing. In this case it is preferred that the entire phase change material does not get transferred to a stable state through an endothermic reaction caused by heating carried out by the hot flowable material, e.g., water, and the resulting complete phase transition, but rather that it preferably goes always back to its initial state before the heating, automatically, by an exothermic reaction. If the phase change material were to experience a complete phase transition through the endothermic reaction, then the phase change material could not be caused to undergo an exothermic phase transition without an external triggering. The hot water bottle latent heat storage means must therefore preferably be designed in such a way that it can be inserted in its initial state, in which an endothermic reaction is possible or still possible, into a hot water bottle. Because a phase change material in this state normally has a solid form, insertion into the hot water bottle requires certain geometric conditions; e.g., the hot water bottle latent heat storage means must fit through the opening of the hot water bottle. Due to the limited opening size of a hot water bottle, the hot water bottle latent heat storage means must have a minimum length or a minimum amount of phase change material to change, not completely, through the hot flowable material, e.g., water, into the above-discussed stable state after an endothermic reaction. There is, for example, a hot water bottle latent heat storage means that has sodium acetate as its phase change material. The phase change material must be at least partially in a crystallised form before being inserted into the hot water bottle, so that the exothermic reaction can occur or be completed. If the phase change material is in a fully liquid state, i.e. it has fully completed the endothermic phase transition, then a triggering of the exothermic phase transition could no longer take place once the hot water bottle latent heat storage means has been inserted into the hot water bottle. The hot water bottle latent heat storage means with the partially and preferable completely crystallised phase change material is inserted into the hot water bottle through the opening of the hot water bottle. When hot water or temperature controlled flowable material is supplied (poured) into in the hot water bottle, the phase change material partially melts by absorbing heat (heat of fusion). It is important that the phase change material does not melt completely and that the latent heat storage means has therefore the appropriate form, e.g., the appropriate thickness, and/or that the phase change material is present in the appropriate amount or mass. By absorbing the heat of fusion, the temperature of the supplied flowable material, e.g., water, is cooled. If the temperature of the supplied flowable material, e.g., water, falls below a certain threshold temperature, e.g., the solidification temperature of the phase change material, then the phase change material will automatically start to solidify, thereby releasing heat to the flowable material, e.g., water, or to the hot water bottle wall.

Furthermore, the thread of the hot water bottle preferably extends in an axial direction by at least 3 mm and more preferably by at least 4 mm, 5 mm, 6 mm, 7 mm, 8 mm, 9 mm, 10 mm or more than 10 mm. The hot water bottle latent heat storage means is also preferably designed in such a way that it cannot be removed from the hot water bottle without the use of a tool or without it being destroyed.

The hot water bottle latent heat storage means is particularly preferably suited as a retrofit means for retrofitting hot water bottles. Preferably the hot water bottle latent heat storage means is shaped in a tubular form. The tubular shaped hot water bottle latent heat storage means preferably has sectionally in a cross section, which is orthogonal to the longitudinal direction of the tubular shaped hot water bottle latent heat storage means, e.g., a round shape. The diameter of the hot water bottle latent heat storage means is preferably smaller or equal to 30 mm, e.g., smaller or equal to 29 mm, e.g., smaller or equal to 28 mm, e.g., smaller or equal to 27 mm, e.g., smaller or equal to 26 mm, e.g., smaller or equal to 25 mm, e.g., smaller or equal to 24 mm, e.g., smaller or equal to 23 mm, e.g., smaller or equal to 22 mm, e.g., smaller or equal to 21 mm, e.g., smaller or equal to 20 mm. The tubular shaped hot water bottle latent heat storage means extends in its axial direction or in its longitudinal direction preferably exactly, at least, or maximally 50 mm, to exactly, maximally, or more than 60 mm, to exactly, maximally, or more than 70 mm, to exactly, maximally, or more than 80 mm, to exactly, maximally, or more than 90 mm, to exactly, maximally, or more than 100 mm, to exactly, maximally, or more than 110 mm, to exactly, maximally, or more than 120 mm, to exactly, maximally, or more than 130 mm, to exactly, maximally, or more than 140 mm, to exactly, maximally, or more than 150 mm, to exactly, maximally, or more than 160 mm, to exactly, maximally, or more than 170 mm, to exactly, maximally, or more than 180 mm, to exactly, maximally, or more than 190 mm, to exactly, maximally, or more than 200 mm, to exactly, maximally, or more than 210 mm, to exactly, maximally, or more than 250 mm, to exactly, maximally, or more than 300 mm, to exactly, maximally, or more than 3500 mm, to exactly, maximally, or more than 4000 mm.

The present teachings may also relate to a hot water bottle with at least one hot water bottle latent heat storage means.

For the purposes of the present teachings, the flowable material is preferably a fluid, e.g., a liquid, a bulk material or a mixture of bulk material and fluid. A preferred fluid in this case is water, but alternatively oil or other liquids or gels or fats or creams can be used. Furthermore, the bulk material should preferably be understood as kernels or seeds. Kernels, in this case, could for example be cherry stones, grape seeds, kernel mixtures etc. Seeds could be flax seeds, for example. Sand, soil, stones, mud etc. are also considered as flowable materials in the light of the present teachings.

The present teachings relate furthermore to a set of the above-described heating device and an exchangeable cover, e.g., a textile cover, wherein the cover encloses at least one section of the flexible wall of the heating device. The set particularly preferably has a closure to open and close the heating device. The cover is preferably made of a material selected from the following group at least consisting of fleece, polymer material such as neoprene, cotton, wool, terry cloth e.g. etc. Particularly preferably, the cover forms two heat insulating parts that vary significantly from each other, wherein the significantly different heat insulating parts are spaced apart by the heating device when the cover covers the heating device. The cover is designed to be in the shape of a shell, into which the heating device could be inserted. It is possible for one part of the cover to be thinner than the other. The parts of the cover are designed in such a way that they are located on opposite and spaced apart wall parts of the heating device and preferably completely cover it or lie on top of it. It has been demonstrated that the effects of such a heating device, e.g., a hot water bottle, are emphasised by the use of a cover.

The use of the word "substantially" is defined preferably in all cases in which this word is used in the context of the present teachings with a deviation in the range of 1%-30%, e.g., of 1%-20%, e.g., of 1%-10%, e.g., of 1%-5%, e.g., of 1%-2%, from the definition that would be understood without the use of this word. Individual or all illustrations of the figures described hereinafter are preferably to be regarded as design drawings, i.e. the dimensions, proportions, functional relationships and/or arrangements shown by the figures preferably correspond exactly or preferably substantially to those of the present teachings device or invented product. Additional benefits, objects and properties of the present teachings will become apparent from the description below attached to the drawings, in which heating devices according to the present teachings are illustrated for exemplary purposes. Elements relating to the means and methods of the present teachings, which in the figures at least substantially match their function, may in this case be identified by the same reference numerals, while these components or elements may not necessarily be quantified or described in all figures. In the following, the present teachings will further be described with reference to the attached figures.

BRIEF DESCRIPTION OF THE DRAWINGS

FIG. 2a shows a sectional view of a heating device according to another preferred embodiment of the present teachings.

FIGS. 2b and 2c show sectional views of various heating devices according to a preferred embodiment of the present teachings, wherein the individual heating devices have different latent heat storage means or different quantities of latent heat storage means.

FIG. 4b shows a top view of the heating device shown in FIG. 4a.

FIG. 6 shows a top view of an at least partially transparent heating device according to another preferred embodiment of the present teachings.

FIGS. 9a and 9b show each showing a further preferred embodiment of the present teachings, with the latent heat storage means showing a large surface area in both illustrations.

FIG. 11a, 11b, 11c show three different views of an exemplary latent heat storage means, e.g., for use in a hot water bottle.

DETAILED DESCRIPTION OF THE INVENTION

Figure 1:
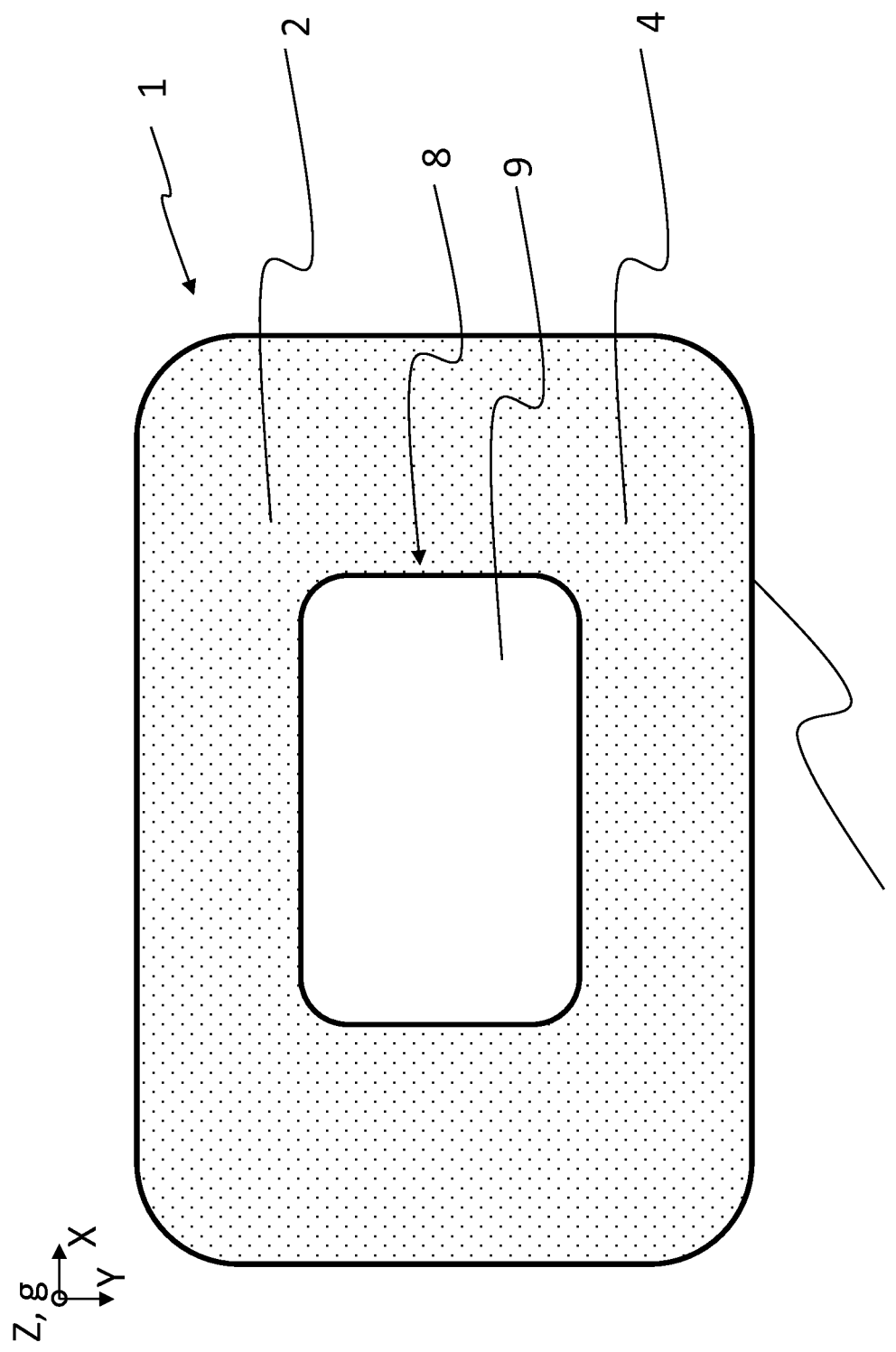
FIG. 1 shows a sectional view of a heating device according to a preferred embodiment of the present teachings.

FIG. 1 shows a first heating device 1 according to the present teachings. The heating device 1 is preferably designed as a heating pad. The heating device 1 has a receiving space 2, which is surrounded or delimited by a wall 6. The wall 6 can be made of rubber, a polymer, e.g., PVC, or of a textile material, e.g., a knitted fabric. The receiving space 2 is at least partially filled with a flowable material 4. The flowable material 4 is preferably a bulk material such as sand, kernels, stones, or a fluid such as water, mud or a gel, etc. One can conclude in this case that the wall of the heating device 1 has been designed/selected in such a way that it can hold the selected flowable material 4 either substantially without loss or without any loss. In the receiving space 2, at least one latent heat storage means 8 is provided next to the flowable material 4 or is surrounded by the flowable material 4. The at least one latent heat storage means 8 can be arranged or placed loosely in the receiving space 2 or it can be positioned with respect to the wall 6 using a fastener or it can be fixed or placed on the wall 6. Reference numeral 9 schematically indicates the interior space of the latent heat storage means 8 which is preferably delimited by a film-like wall. In the interior space 9 of the latent heat storage means, there is a phase change material.

In FIG. 2a a sectional view of the heating device 1 is shown in its preferred form as a hot water bottle. This heating device 1 has at least or exactly one filling/emptying opening 12. The filling/emptying opening 12 can preferably be closed by a closure (stopper) 14. The closure 14, depending on the configuration of the filling/emptying opening 12, can have an external thread or an internal thread or can be designed with any other sealing closure concept.

FIGS. 2b and 2c show sectional views with the sections taken along the Y-Z plane. FIG. 2b shows a latent heat storage means 8 within a receiving space 2. FIG. 2c shows several latent heat storage means 8 arranged within the receiving space 2. One can deduce from this that the latent heat storage means 8 shown in FIG. 2c together have a larger surface area than the latent heat storage means 8 shown in FIG. 2b, wherein the latent heat storage means 8 shown in FIG. 2b, for an equal length extending in the X direction or in the longitudinal direction of the heating device 1, holds or can hold a larger amount of phase change material.

Figure 3B:
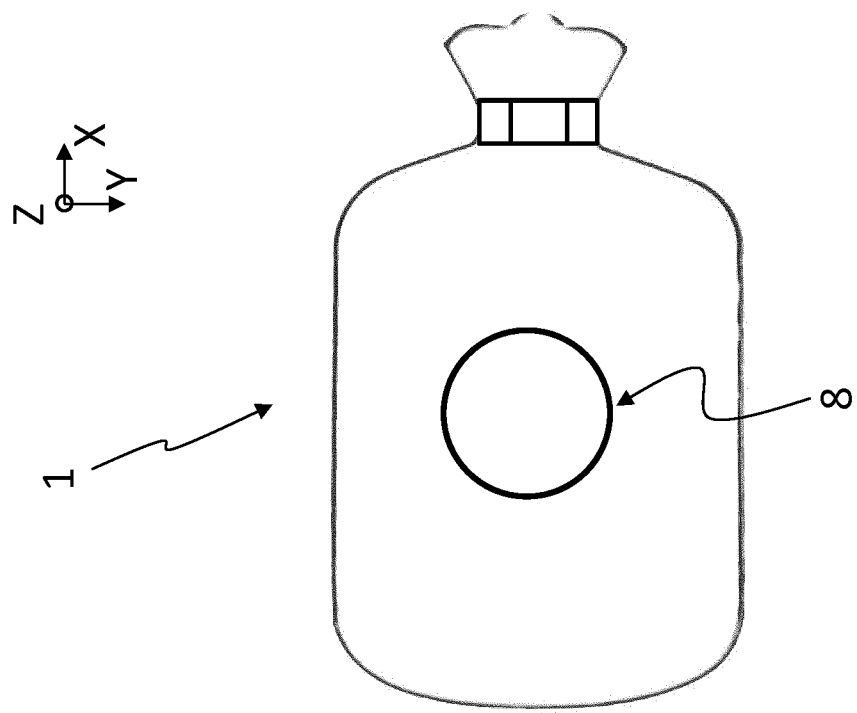
FIGS. 3a and 3b show sectional views of various heating devices according to a preferred embodiment of the present teachings.
Figure 3A:
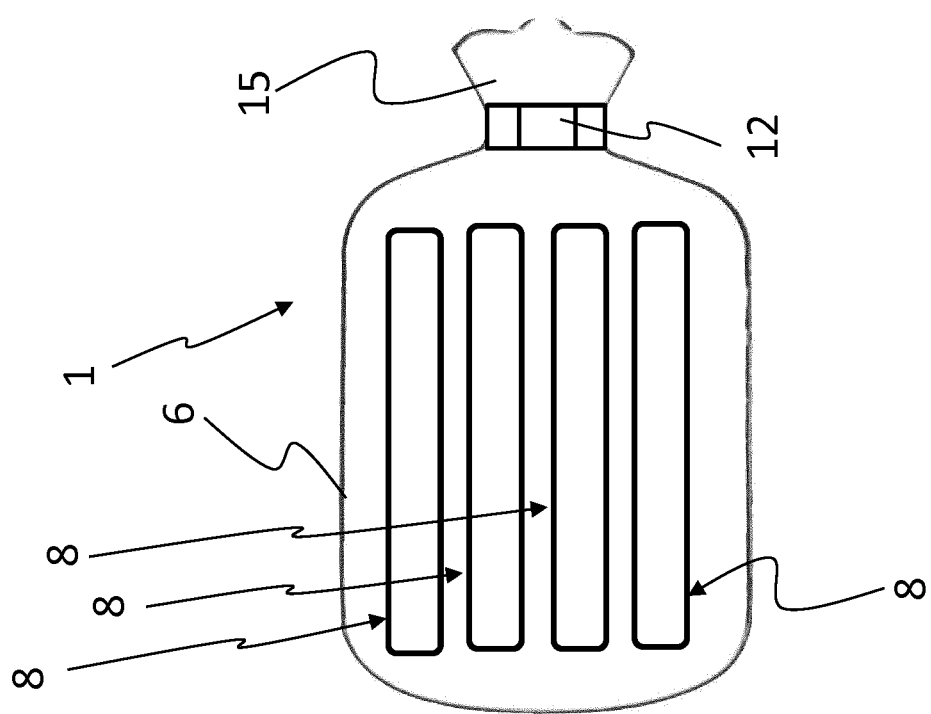

In the illustrations shown in FIGS. 3a and 3b, the heating devices 1 have a funnel 15 for simplifying the filling of the flowable substance. It is however also possible in this case that the illustrated heating devices 1 are also designed without such a funnel 15. Furthermore, it is conceivable that all heating devices 1 shown in all the following figures, which have a filling/emptying opening 12 or an inlet and outlet means 12, may have such a funnel 15. Furthermore, the respective illustrated filling/emptying openings 12 that are shown in the various embodiments disclosed herein are simply examples.

From FIG. 3a it is evident that several latent heat storage means 8 are located within the receiving space 2. It is thus conceivable that at least or exactly two, at least or exactly three, at least or exactly four, at least or exactly five, at least or exactly six, at least or exactly seven latent heat storage means 8 can be provided or inserted or arranged within one receiving space 2.

FIG. 3b shows an embodiment in which the latent heat storage means 8 is shaped spherical or substantially spherical, e.g., disc or ball shaped.

Figure 4B:
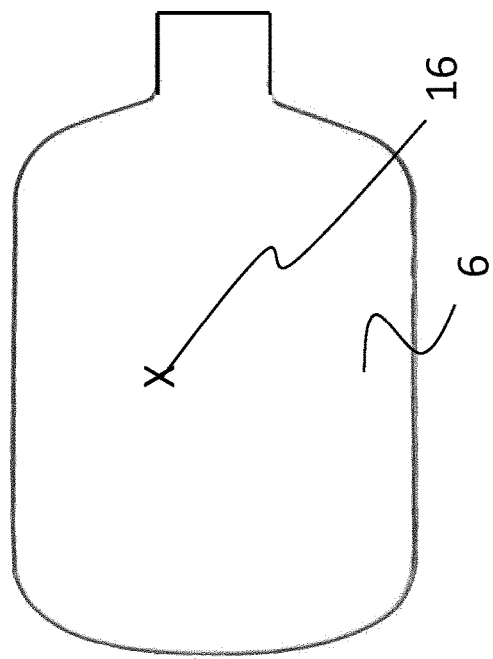
Figure 4D:
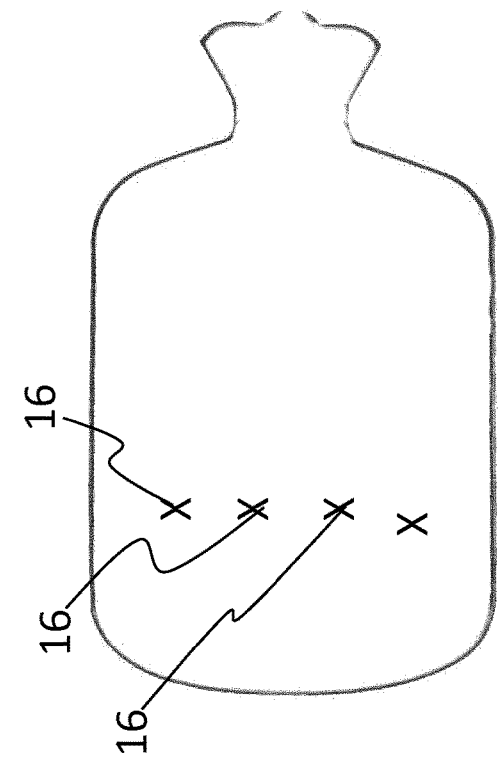
FIG. 4d shows a top view of the heating device shown in FIG. 4c.
Figure 4A:
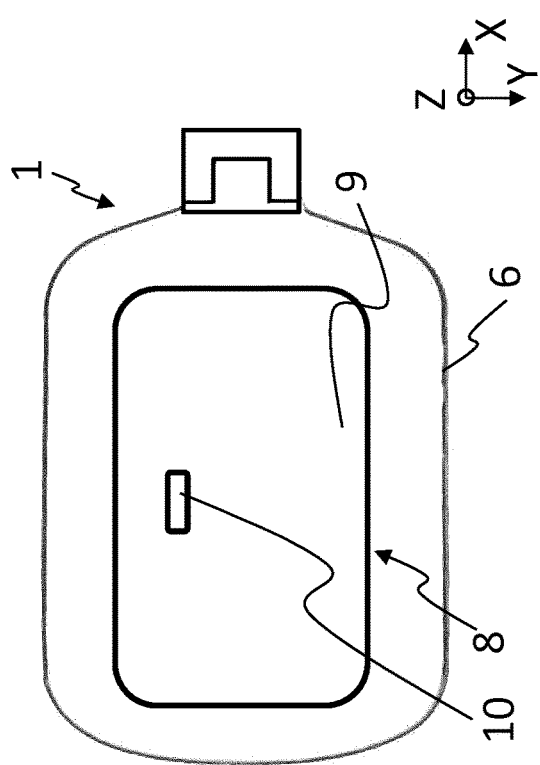
FIG. 4a shows a sectional view of a heating device according to another preferred embodiment of the present teachings.

FIG. 4a shows a heating device 1 that is preferably designed as a hot water bottle. This heating device 1 has at least one latent heat storage means 8. The latent heat storage means 8 includes an actuating means 10, e.g., a metal spring or a clicker, for triggering the exothermic phase transition of the phase change material. Preferably, in this embodiment, the actuating means 10 and/or the latent heat storage means

8 is always located in a defined manner with respect to a wall portion 6 of the heating device 1, e.g., opposite a marking (compare to FIG. 4*b*) made with respect to or planned on the wall portion 6.

It is also conceivable that one or at least one latent heat storage means 8 with an actuating means 10 is located within a heating device 1 designed as a heating pad. In this case the actuating means 10 is preferably also located in a defined manner with respect to a wall portion 6 of the heating device 1.

FIG. 4*b* shows a top view of a heating device 1. It can be seen in this illustration a marking 16 is provided on the wall 6. This marking 16 preferably shows the position or substantially the position of the actuating means 10.

Figure 4C:
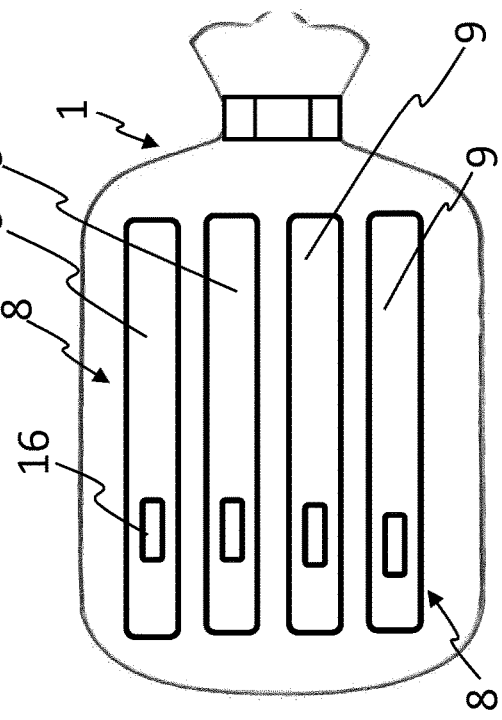
FIG. 4c shows a sectional view of a heating device according to another preferred embodiment of the present teachings.

FIGS. 4*c* and 4*d* show a similar example to FIGS. 4*a* and 4*b*, with FIGS. 4*c* and 4*d* showing more latent heat storage means 8 and therefore more markings 16. It is preferably conceivable here, that the number of markings 16 correlates to the number of actuating means 10.

Figure 5C:
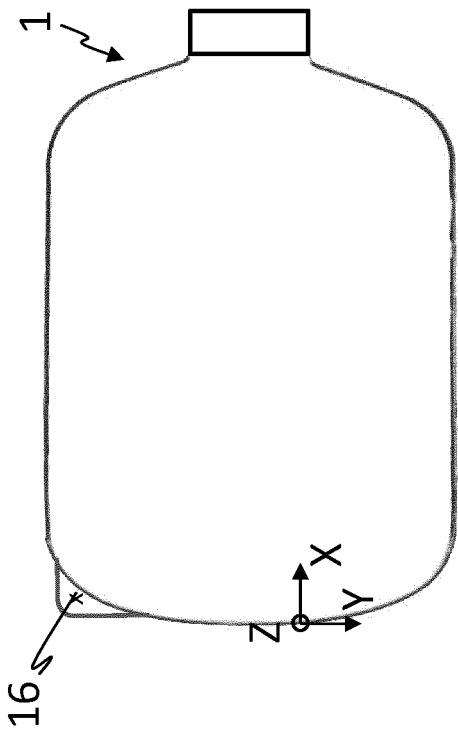
FIG. 5c shows a top view of the heating device shown in FIGS. 5a and 5b.
Figure 5D:
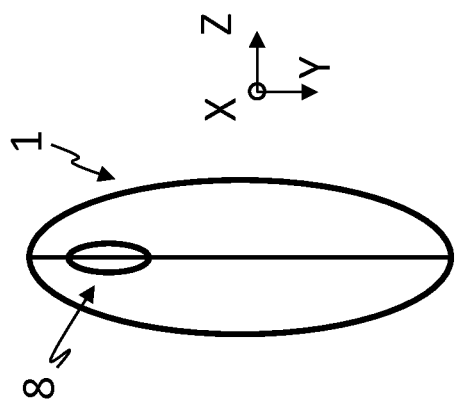
FIG. 5d shows a rear view of the heating devices shown in FIGS. 5a to 5c.
Figure 5A:
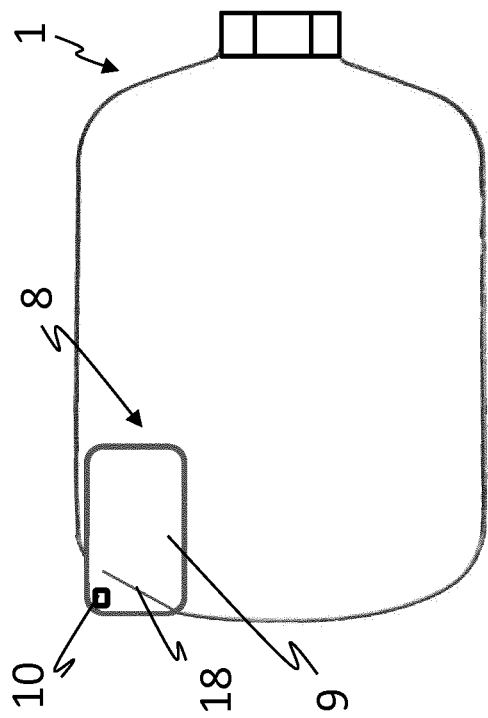
FIGS. 5a and 5b show sectional views of various heating devices according to another preferred embodiment of the present teachings.

FIG. 5*a* shows a sectional view of an embodiment, in which a part of the latent heat storage means 8 is located outside of the receiving space 2. In the area outside of the receiving space 2 where the latent heat storage means 8 is located, an actuating means 10 is preferably also arranged. The part of the latent heat storage means 8 outside the receiving space 2 is preferably separated from the part of the latent heat storage means 8 within the receiving space 2 so that the actuating means 10 is preferably exclusively located outside the receiving space 2. It is preferable that at least the part of the latent heat storage means 8, in which the actuating means 10 is arranged, is partially or completely transparent. Furthermore, the part of the latent heat storage means 8 located outside the receiving space 2 is separated from the part of the latent heat storage means 8 located within the receiving space 2 in such a way that the exothermic phase transition and the endothermic phase transition of the phase change material located in the interior space 9 of the latent heat storage means 8 can preferably happen completely. Furthermore, reference numeral 18 depicts a separation which can form as e.g. a gap as shown in FIG. 5*a* or—as shown in FIG. 5*b*—e.g. by a kind of perforation.

Furthermore, it is conceivable that a heating device 1 may have several latent heat storage means 8 that are arranged in such a way that they are contactable by a user while the heating device 1 is closed. Preferably, the heating device 1 designed e.g., as a hot water bottle, has several, e.g., at least, exactly or no more than 2, at least, exactly or no more than 3, at least, exactly or no more than 4, at least, exactly or no more than 5, at least, exactly or no more than 6 latent heat storage means 8, which are contactable by a user while the heating device 1 is closed or which extend beyond the receiving space 2.

FIG. 5*c* shows a top view of a heating device 1 according to the present teachings, which preferably has a marking 16 in the area of the latent heat storage means 8 or preferably on the latent heat storage means 8, thereby marking the position of the actuating means 10. It is, however, also conceivable that no marking 16 is necessary because the spatial differentiation of the area, in which the actuating means 10 is located, makes it obvious where the actuating means 10 is located. Furthermore, it is conceivable that the latent heat storage means 8 is at least partially transparent or transparent in such a way that it is recognisable where he actuating means 10 is located.

Figure 5B:
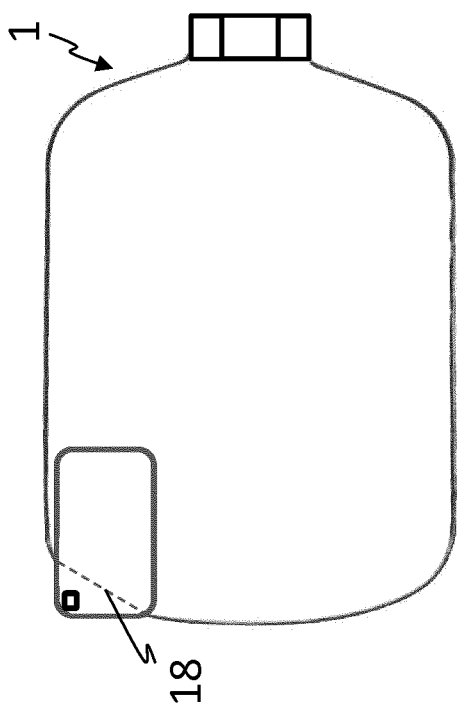

FIG. 5*d* shows a rear view of the heating device 1 shown in FIGS. 5*a* to 5*c*. In FIG. 5*d*, a seam that was created during the manufacture of the heating device, e.g., using a blow mould or during vulcanisation, can be seen.

FIG. 6 shows a top view of a heating device 1 that is at least partially and preferably substantially, or more preferably completely, transparent on one or both sides. Due to the transparency of the wall, the location of the latent heat storage means 8 and the actuating means 10 in it are visible. The latent heat storage means 8 is preferably also transparent on at least one side and preferably both sides and is at least partially and preferably substantially or more preferably completely transparent.

Figure 7:
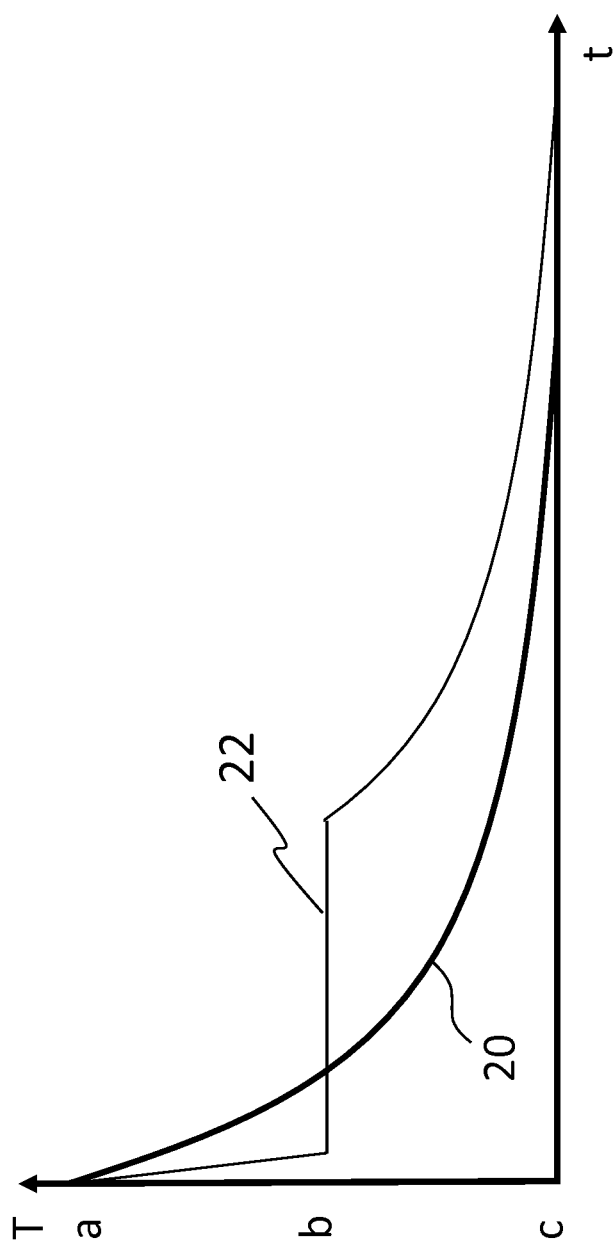
FIG. 7 shows a normal cooling curve and a cooling curve in the sense of the present teachings.

FIG. 7 shows two different schematic temperature profiles 20 and 22. The temperature profile 20 substantially shows a cooling down of a conventional heating device and the temperature profile 22 substantially shows a cooling down of the heating device according to the present teachings.

According to both curves, the heating device 1 is temperature controlled (i.e. heated) to a starting temperature a, e.g., a temperature between 60° C. and 100° C. and preferably 95° C. or substantially 95° C. The heating can take place by filling the heating device 1 with a hot flowable material 4, e.g., hot water. In contrast to the conventional temperature profile 20, the flowable material cools off faster at first in the heating device 1 of the present teachings. The faster cooling down is caused by the transfer of heat from the flowable material 4 to the latent heat storage means 8, which is located inside the receiving space 2 or on the receiving space 2 or on the wall 6 of the receiving space 2, in the heating device 1. Due to the heat transfer, the phase change material, located in the latent heat storage means 8, undergoes a partial endothermic phase transition. When the flowable material cools off to or below the threshold (e.g., melting) temperature of the phase change material, an exothermic phase transition begins to take place. The phase change material continues to release the energy absorbed during the endothermic phase transition, in the form of heat, until the phase change material returns to its original state, e.g., as a solid body. Owing to the heat release of the phase change material, the cooling curve is modified or the flowable material is temperature controlled, which means that it maintains a constant or substantially constant temperature for a certain period of time. Both curves 20, 22 eventually cool down to the ambient (room) temperature c, e.g., 20° C. The latent heat storage means 8 is therefore preferably designed in such a manner that with a defined amount, e.g., a complete filling of the receiving space 2, of a defined temperature controlled, e.g., at 95° C., flowable material, e.g., water, the phase change material only undergoes a partial endothermic phase transition, and that e.g., the phase transition is automatically reversed to its original state before the phase transition.

The temperature profile described in FIG. 7 occurs particularly preferably in the embodiments shown in FIGS. 2*a*-2*c* and 3*a*-3*b*.

Figure 8A:
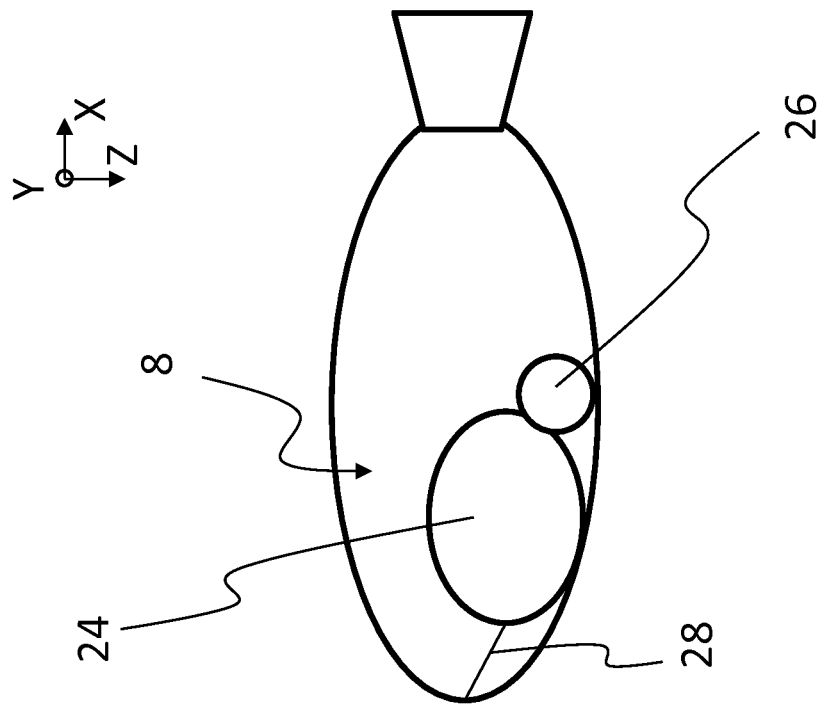
FIGS. 8a and 8b show another preferred embodiment of the present teachings, according to which the latent heat storage means is preferably fixed to a wall limiting the receiving space.

FIG. 8*a* shows a cross-sectional view of a heating device 1 according to the present teachings with a modified latent heat storage means 8. The hot water bottle latent heat storage means or the latent heat storage means 8 has several chambers 24 and 26 in which phase change material is located. The chambers 24, 26 are functionally or physically connected to each other in such a way that an exothermic phase transition triggered in the main chamber 24 passes to the other chamber(s), i.e. the secondary chamber(s) 26. This embodiment has the advantage that one or several secondary chambers 26 can be provided, for example in a cooling fin manner, to create the largest possible heat transfer surface. However, the main chamber 24 is preferably designed in such a way that the phase change material contained within it, during a maximum heat supply, through the supply of temperature controlled flowable material, only partially undergoes an endothermic phase transition. The phase change material located in the secondary chamber(s) can, however, undergo a complete phase transition. The secondary chamber(s) 26 preferably has/have a different "surface to phase change material amount" ratio compared to the main chamber 24, with the main chamber 24 preferably having a smaller surface area with the same amount of phase change material. It is, however, conceivable that all the secondary chambers 26 together have more phase change material and together have a larger surface area than the main chamber 25.

The reference numeral 28 identifies a preferably flexible fixation element. The fixation element 28 is preferably used to attach the latent heat storage means 8 to the wall 6 of the heating device 1. The fixation element 28 preferably comprises plastic. Particularly preferably, the fixation element 28 is a component of the latent heat storage means 8. It must be expressly pointed out that the fixation element 28 has only been attached to a latent heat storage means 8 which has a secondary chamber 26, as an example. It is also conceivable that it is attached to a latent heat storage means 8 or materialized on a latent heat storage means 8 that has no or several secondary chambers 26. Preferably, the fixation element 28 is connected to the wall 6 of the heating device 1 during the manufacture of the heating device 1 in the preferable form of a hot water bottle. The benefit of the fixation element 28 is that it preferably prevents the clogging of the outlet of the latent heat storage means 8 when the flowable material of the heating device 1, which is preferably embodied as a hot water bottle, is poured out.

Figure 8B:
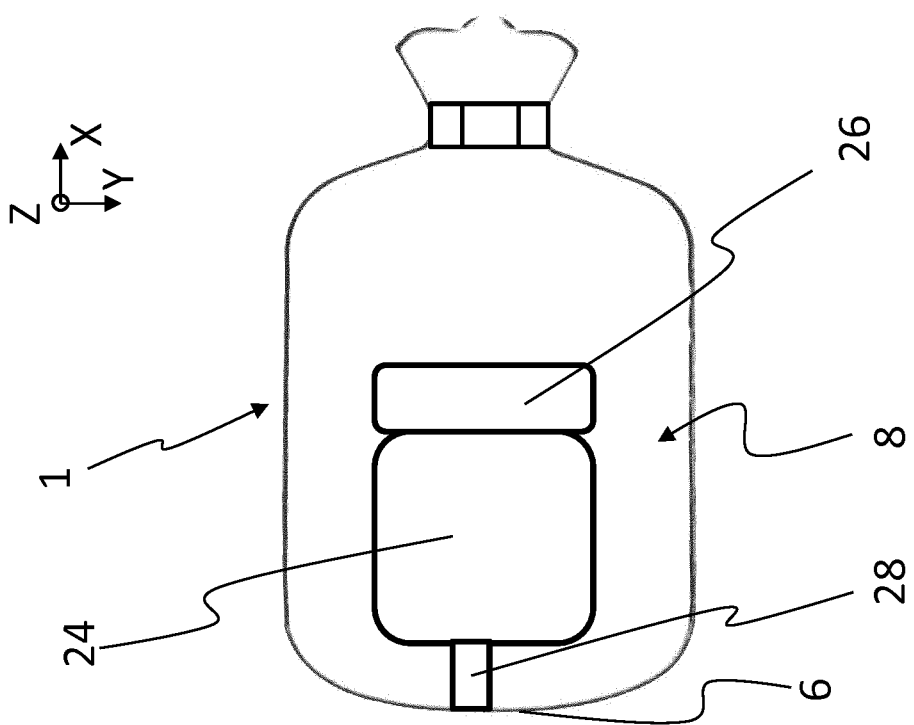

Merely as an example, FIG. 8b shows a side view of the sectional view of the heating device 1 shown in FIG. 8a.

FIG. 9a shows a cross-sectional view of a heating device 1. The latent heat storage means 8 shown can extend in a different plane, for example in the same way as the latent heat storage means 8 shown in FIG. 2a or in FIG. 6. The latent heat storage means 8 is characterised in that its surface area, as compared to its volume, is relatively large. Preferably, the latent heat storage means 8 has two or more, e.g., three or more, four or more, five or more retention areas which overlap each other and at least partially extend on parallel planes, in which a phase change material is located. Preferably at least two and preferably at least three and particularly preferably at least 4, 5, 6, or more or all retention areas that overlap each other or are interconnected to permit fluid communication.

Herein, "fluid communication" preferably means that a crystallisation or solidification or hardening or phase change (from liquid to solid) happening in one retention area can transfer or transfers to another retention area 32. That is, "fluid communication" particularly preferably means that the phase change material is in a state where the material is able to flow and is partially transferable or conductible from one retention area 32 into another retention areas 32. The wall of the latent heat storage means 8 is thus preferably the wall of the retention area 32. The wall of the latent heat storage means 8 is preferably flexible, and the wall is preferably made of a polymer.

The latent heat storage means 8 particularly preferably has spacing elements 28 that are located or that are arrangeable between the individual retention areas 32 of the latent heat storage means 8.

The spacing elements 28 are preferably stuck to the wall of the latent heat storage means 8. It is however also conceivable that the spacing elements 28 form part of the wall of the latent heat storage means 8. Furthermore, it is conceivable that at least two retention areas are in fluid communication with each other through at least one spacing means 28.

It is furthermore conceivable that individual wall parts of the latent heat storage means 8, e.g., of the individual retention areas 32, are connected to each other via form holding elements 33 or form retaining elements 33, with a form holding element 33 or one form retaining element preferably limiting an expansion of the volume, locally limited by the walls. The form holding elements 33 therefore preferably prevent the phase change material, which is able to flow, from being conductible from one retention area to another retention area that would result in a significant increase of the amount of phase change material in one retention area and a significant decrease in another retention area. The form holding elements 33, which may be locally stuck in weldings of the limiting wall parts of a retention area, thus ensure that each retention area substantially holds the desired amount of phase change material. Furthermore, FIG. 9a shows that the spacing elements 28 create a heat transfer area 30 which is located within the outer perimeter of the latent heat storage means 8. The heat transfer area 30, when used, is at least partially filled with the temperature controlled (heated) flowable material.

FIG. 9b shows another conceivable embodiment of the latent heat storage means 8. According to this embodiment, the latent heat storage means 8 can have several uniform and preferably also several therefore differently formed chambers 24, 26, with preferably all chambers 24, 26 being in fluid communication with each other. Furthermore, FIG. 9b shows that the heat transfer area 30 between the individual retention areas 32 is formed by the shape of the individual chambers 24, 26. Wherein the volume of the interior space of the latent heat storage means 8 should thus preferably consist of the volumes delimited by the retention areas 32.

The latent heat storage means 8 shown in FIGS. 9a and 9b are ideally shown located in the centre of the heating device 1. In one state of use, they are however preferably located at a section of the wall 6 that delimits the receiving space 2. It is furthermore conceivable that the latent heat storage means 8 shown in FIGS. 9a and 9b are combined with each other or that two or more different latent heat storage means 8 are used in one heating device or that at least one latent heat storage means 8 is created that has the properties of many (not only those shown in FIGS. 9a and 9b) of the latent heat storage means described herein.

FIGS. 9a and 9b thus each show one latent heat storage means 8 that can be used in a heating device 1, e.g., a hot water bottle. The latent heat storage means 8 here preferably comprises of at least an interior space delimited by a flexible wall for holding a phase change material, wherein the phase change material absorbs energy during an endothermic phase transition and releases energy in the form of heat during an exothermic phase transition, whereby the flexible wall is designed such that a first part of the interior space extends in one plane and the second part of the interior space extends at least partially and preferably fully in a second plane, whereby the first plane and second plane are parallel to each other, and wherein a heat transfer area is formed or formable between the first part of the interior space and the second part of the interior space, through which heat is transferable to the phase change material from the temperature controlled (hot) flowable material. The wall of the latent heat storage means 8 preferably consists partially and preferably completely of a waterproof material, e.g., a polymer and/or a membrane.

Figure 10:
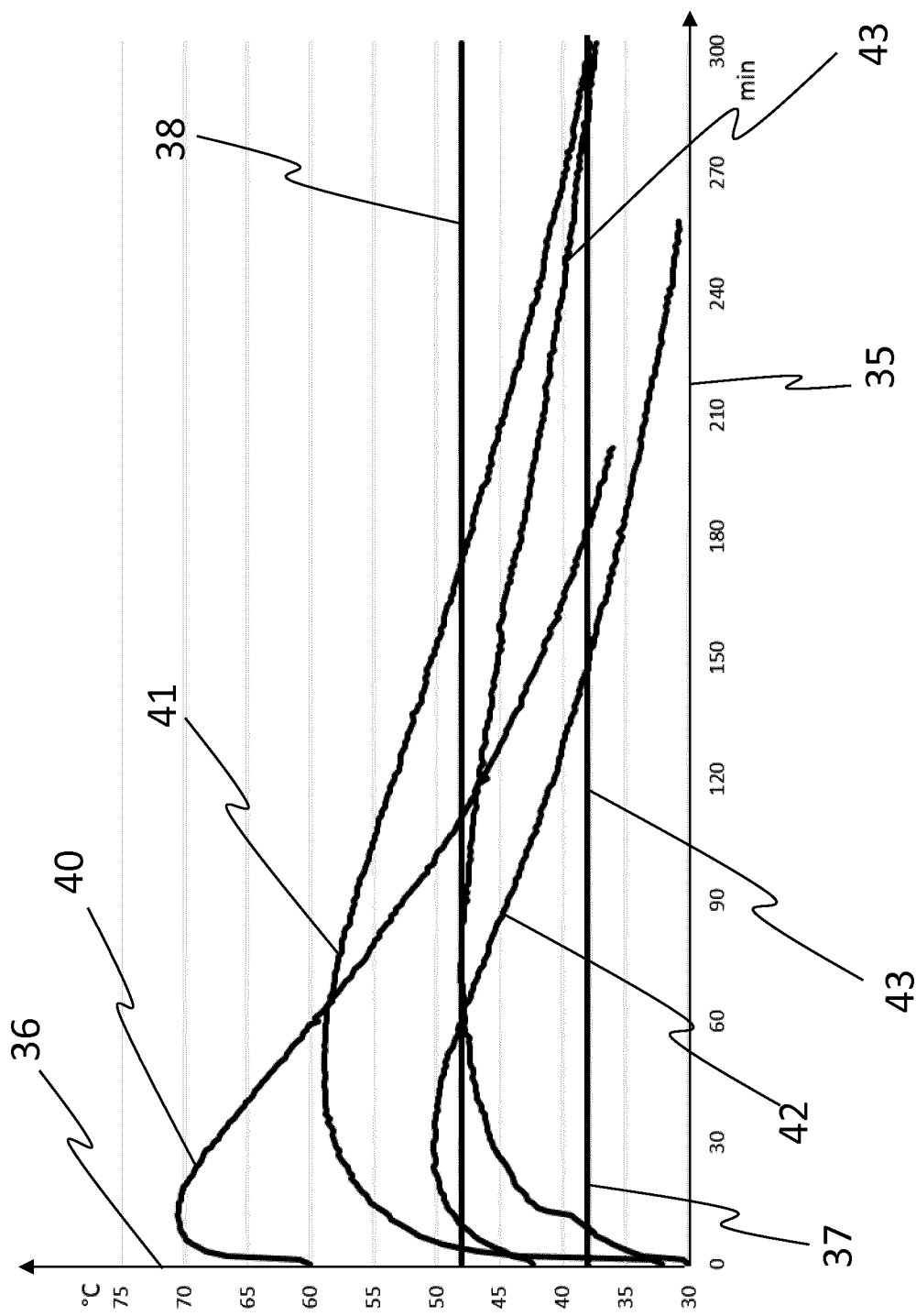
FIG. 10 shows a diagram showing the cooling curves of the different hot water bottle configurations.

FIG. 10 shows a diagram in which the time in minutes is displayed on the X-axis 35, and the temperature in ° C. is displayed on the Y-axis 36. Line 37 indicates a lower limit of an optimal heat range and line 38 indicates the upper limit of an optimal heat range. The lower limit of the optimal heat range is 38° C. in this illustration and the upper limit of the optimal heat range in this illustration is 48° C. Reference numerals 40, 41, 42, 43 indicate the cooling curves of various hot water bottle configurations, wherein the boundary conditions are identical or at least comparable, i.e. the same hot water bottle shape, the same hot water bottle material, the same room temperature, the same measurement method and an equal heating of the water poured into the hot water bottle (poured into the hot water bottle at 80° C.). The diagram shows that the surface temperature of a classic hot water bottle without a cover (cooling curve 40) remains above the upper limit 38 of the optimal heat range about two times longer than a hot water bottle according to the present teachings without a cover (cooling curve 42). The surface temperature of a classic hot water bottle with a cover (cooling curve 41), such as a neoprene and/or fleece cover, stays even longer above the upper limit 38 of the optimal temperature range. It can thus be seen that there is a great risk of burns with (classic) hot water bottles that cool off according to curves 40 and 41. Furthermore, the diagram shows that the surface temperature of a heating device (cooling curve 43) according to the present teachings, e.g., the hot water bottle, with a cover, e.g., a neoprene and/or fleece cover, remains in the optimal heat range for the longest time, particularly by at least a factor of 2 longer in the optimal heat range as compared to the other tested variants.

FIG. 11*a* shows a cross-section of a latent heat storage means 8. The cross-section corresponds to the section marked with the letter A in FIG. 11*b*. Reference numeral 32 here indicates the retention area in which the phase change material is received or retained. Reference numeral 33 here indicates a form holding element which in this illustration acts as a strut-like configuration of the latent heat storage means 8. The form holding element 33 prevents the latent heat storage means 8 from deforming so that the latent heat storage means 8 does not bulge out locally as a result of moved phase change material. The form holding elements 33 also ensure that the surface area of the latent heat storage means, which is delimited by the retention area 32, is larger than without these form holding elements 33.

FIG. 11*b* shows a top view of the latent heat storage means 8 and FIG. 11*c* shows a perspective view of the latent heat storage means 8.

According to respective embodiments illustrated in FIGS. 1 to 11*c*, the latent heat storage means 8 can be designed, additionally or preferably alternatively, in such a way that, with a defined amount, e.g., a full filling of the receiving area 2 with a defined temperature controlled (hot) flowable material, e.g., at 95° C., e.g., water, the phase change material can undergoe a complete endothermic phase transition.

According to respective embodiments illustrated in FIGS. 1 to 11*c*, the latent heat storage means 8 can have, additionally and alternatively, preferably an actuating means 10, e.g., a clicker preferably comprising at least one metal, to trigger the exothermic phase transition.

According to respective embodiments illustrated in FIGS. 1 to 11*c*, the latent heat storage means 8 can have, additionally or alternatively, preferably an actuating means 10, e.g., a metal device preferably containing at least two metals, e.g., a bimetallic device, such as a bimetallic strip, to trigger the automatic exothermic phase transition. The actuating means 10 is preferably designed in such a way that it deforms in accordance with the temperature. This is beneficial because the actuating means 10 automatically triggers during the cooling of a phase change material, which has been transformed into a liquid form, to a temperature below the solidification temperature of the phase change material, through a form change, a phase change of the phase change material, e.g., by nucleation or through a nucleus release.

According to respective embodiments illustrated in FIGS. 1 to 11*c*, the latent heat storage means 8 can be designed, additionally or alternatively, in such a way that, with a defined amount, e.g., a full filling of the receiving area 2, and with a defined temperature controlled flowable material, e.g., at 95° C., e.g., water, the phase change material only undergoes a partial endothermic phase transition.

The present teachings therefore relate to a heating device 1, e.g., a hot water bottle or a heating pad, which at the very least will have indirect contact with a living being. The heating device comprises at least one receiving space 2 for holding flowable material 4, wherein the receiving space 2 is at least partially sectioned off with a flexible wall 6 and the flexible wall 6, at the very least, can be brought into indirect contact with the living being. According to the present teachings, a latent heat storage means 8 is provided, wherein the latent heat storage means 8 is arranged in such a manner that at least some of the time a temperature control of the flowable material 4 therewith, wherein the latent heat storage means 8 has a phase change material, e.g., sodium acetate, wherein the phase change material to absorb energy during an endothermic phase transition due to warming and release energy during an exothermic phase transition in the form of heat. Thereby, flowable material is preferably added to the heating device at a temperature higher than 60° C., 70° C., 80° C., 90° C. and up to 95° C., e.g., with a temperature between 60° C. and 100° C. or between 70° C. and 100° C. or between 80° C. and 100° C. or between 90° C. and 100° C. or brought to this temperature within it. The filling of the heating device with the flowable substance should preferably lie between 40% and 100%, e.g., between 50% and 100% or 60% and 100% or 70% and 100% or 80% and 100% or 90% and 100%. With the latent heat storage means being designed in such a way or having so much phase change material, the phase change material at the previously mentioned temperature of the flowable substance and the previously mentioned filling amount of water and preferably at an ambient temperature of 20° C. or of 25° C. or of 30° C. or of 40° C. is not completely or only partially transformable from its first stable state, in which the phase change material is preferably solid-like or solid, to a second state, in which the phase change material is liquid.

The phase change material is preferably an inorganic material, e.g., a salt based material. The phase change material is particularly preferably a material that is convertible from an original stable physical state (solid) to a second meta-stable physical state (liquid).

The latent heat storage means is preferably designed such that, e.g., when it does not comprise an actuating means, the phase change material parts contained within it interact functionally, and e.g., cause a nucleus present in a material part of the phase change material to trigger an exothermic phase change of the entire phase change material. The latent heat storage means is particularly preferably designed in such a way that the phase change material parts contained within it interact functionally, wherein nucleus present in the material part of the phase change material triggers an exothermic phase change of the entire phase change material when the temperature of the flowable material falls below the solidification temperature or melting temperature of the phase change material. The amount or mass of phase change material is preferably such that, in an embodiment without an actuating means and wherein the receiving space is filled to at least ⅔rds with a flowable material that is at a temperature above the melting point of the phase change material, the endothermic phase transition of the phase change material at an ambient temperature of 20° C. only occurs partially. In other words, the amount or mass of the phase change material is such that an endothermic phase transition of the phase change material only occurs partially when the receiving space at an ambient temperature of 20° C. is at least ⅔rds filled with a temperature controlled flowable material and when the flowable material is heated to a temperature above the melting point of the phase change material.

LIST OF REFERENCE NUMERALS

1 Heating device
2 Receiving space
4 Flowable material
6 Flexible wall
8 Latent heat storage means
9 Interior space of the latent heat storage means
10 Actuating means
12 Filling/emptying opening
14 Closure
15 Funnel
16 Marking
18 Delimiting device
20 Normal cooling curve
22 Modified cooling curve
24 Main chamber
26 Secondary chamber
28 Spacing element
30 Heat transfer area
32 Retention area
33 Form holding element
35 X-axis to show the time
36 Y-axis to show the temperature
37 Lower temperature limit of the optimum temperature range
38 Upper temperature limit of the optimum temperature range
40 Cooling curve of a classic hot water bottle filled with water
41 Cooling curve of a classic hot water bottle with neoprene cover
42 Cooling curve of the hot water bottle of the present teachings
43 Cooling curve of the hot water bottle of the present teachings with neoprene cover
A Section
T Temperature
X first direction/length
Y second direction/depth
Z third direction/height
a Starting temperature
b Constant temperature
c End temperature
g Gravity
t Time

The invention claimed is:

1. A hot water bottle, comprising:
a receiving space defining a first volume for holding water and being formed at least by two blank plates that at least partially define a flexible outer wall of the hot water bottle configured to at least indirectly contact a living being,
a latent heat storage means for at least temporarily controlling a temperature of water in the receiving space, the latent heat storage means being disposed inside the receiving space and including a second volume for holding a phase change material having a property of absorbing energy during an endothermic phase transition when warmed by the water and releasing energy in the form of heat during an exothermic phase transition when the temperature of the water falls below a phase transition temperature of the phase change material,
a filling and emptying opening in fluid communication with the receiving space, and
a thread defined in the filling and emptying opening and configured to threadably engage a threaded closure that closes and seals the filling and emptying opening to seal water within the receiving space,
wherein:
the latent heat storage means is configured such that, when a defined amount of temperature controlled water is placed in the receiving space, the phase change material completely undergoes the endothermic phase transition,
the phase change material is an inorganic material that comprises sodium acetate trihydrate,
the latent heat storage means further includes an actuating means for triggering the exothermic phase transition of the inorganic material,
the latent heat storage means includes a housing that holds the phase change material, the housing defining a plurality of fluidly connected chambers that hold the phase change material,
an entire outer surface of the housing of the latent heat storage means that surrounds the phase change material is in direct contact with the water during usage,
the latent heat storage means is configured to be irremovable from the receiving space,
the housing is formed as a flexible film composed of a polymer material, and
a ratio of the first volume of the receiving space to the second volume is between 2:1 and 7:1.

2. The hot water bottle according to claim 1, wherein the latent heat storage means is formed such that when the temperature of the water falls below the phase transition temperature of the phase change material:
the phase change material contained within the plurality of fluidly connected chambers functionally interacts, and
nucleation in one portion of the phase change material triggers an exothermic phase change throughout the phase change material.

3. The hot water bottle according to claim 1, wherein the housing of the latent heat storage means is attached to the flexible wall or is a part of the flexible wall.

4. The hot water bottle according to claim 1, wherein the ratio of the first volume to the second volume is between 2.5:1 and 5:1.

5. The hot water bottle according to claim 1, wherein the phase change material is solid at 20° C.

6. The hot water bottle according to claim 5, wherein:
the latent heat storage means is formed such that when the temperature of the water falls below the phase transition temperature of the phase change material (i) the phase change material contained within the plurality of fluidly connected chambers functionally interacts, and (ii) nucleation in one portion of the phase change material triggers an exothermic phase change throughout the phase change material;
and the ratio of the first volume to the second volume is between 2.5:1 and 5:1.

7. A hot water bottle, comprising:
a receiving space defining a first volume for holding water and being formed at least by two blank plates that at least partially define a flexible outer wall of the hot water bottle configured to at least indirectly contact a living being,
a latent heat storage means for at least temporarily controlling a temperature of water in the receiving space, the latent heat storage means being disposed inside the receiving space and including a second volume for holding a phase change material that comprises sodium acetate trihydrate, the phase change material having a property of absorbing energy during an endothermic phase transition when warmed by the water and releasing energy in the form of heat during an exothermic phase transition when the temperature of the water falls below a phase transition temperature of the phase change material,
a filling and emptying opening in fluid communication with the receiving space, and
a thread defined in the filling and emptying opening and configured to threadably engage a threaded closure that closes and seals the filling and emptying opening to seal water within the receiving space,
wherein:
the latent heat storage means is configured such that, when at least two-thirds of the first volume of the receiving space is filled with water that is at a temperature above the phase transition temperature of the phase change material and the phase change material is initially at a temperature of 20° C., less than all of the phase change material undergoes endothermic phase transition,
the latent heat storage means has a housing that holds the phase change material, the housing defining a plurality of fluidly connected chambers that hold the phase change material,
an entire outer surface of the housing of the latent heat storage means that surrounds the phase change material is in direct contact with the water during usage,
the latent heat storage means is configured to be irremovable from the receiving space,
the housing is formed as a flexible film composed of a polymer material, and
a ratio of the first volume of the receiving space to the second volume is between 2:1 and 7:1.

8. The hot water bottle according to claim 7, wherein the latent heat storage means is formed such that when the temperature of the water falls below the phase transition temperature of the phase change material:
the phase change material contained within the plurality of fluidly, connected chambers functionally interacts, and
nucleation in one portion of the phase change material triggers an exothermic phase change throughout the phase change material.

9. The hot water bottle according to claim 7, wherein the housing of the latent heat storage means is attached to the flexible wall or is a part of the flexible wall.

10. The hot water bottle according to claim 7, wherein the phase change material is an inorganic material.

11. The hot water bottle according to claim 7, wherein the phase change material is solid at 20° C.

12. The hot water bottle according to claim 11, wherein:
the latent heat storage means is formed such that when the temperature of the water falls below the phase transition temperature of the phase change material (i) the phase change material contained within the plurality of fluidly connected chambers functionally interacts, and (ii) nucleation in one portion of the phase change material triggers an exothermic phase change throughout the phase change material;
and the ratio of the first volume to the second volume is between 2.5:1 and 5:1.

13. A set comprising:
the hot water bottle of claim 7, and
a replaceable cover that encloses at least a portion of the flexible wall.

14. The set according to claim 13, wherein the phase change material has a melting temperature of between 45° C. and 63° C.

15. A set comprising:
the hot water bottle of claim 1, and
a replaceable cover that encloses at least a portion of the flexible wall.

16. The set according to claim 15, wherein:
the phase change material has a melting temperature of between 45° C. and 63° C.

17. A method for manufacturing a hot water bottle configured to be brought in at least indirect contact with a living being, comprising:
preparing two blank plates for forming a receiving space having a first volume, at least one of the two blank plates being configured to at least partially form a flexible outermost wall of the hot water bottle, wherein a filling and emptying opening is in fluid communication with the receiving space and includes a thread for attaching a threaded closure that closes and seals the filling and emptying opening,
placing at least one latent heat storage means between the two blank plates, the latent heat storage means comprising:
a housing formed as a flexible film composed of a polymer material and defining a plurality of fluidly connected chambers, and
a second volume of phase change material disposed in the plurality of fluidly connected chambers of the housing, the phase change material being an inorganic material that comprises sodium acetate trihydrate and has a property of absorbing energy during an endothermic phase transition when warmed by water and releasing energy in the form of heat during an exothermic phase transition when the temperature of the water falls below a phase transition temperature of the phase change material, and
connecting the two blank plates to each other with the at least one latent heat storage means disposed between two blank plates,
wherein: the latent heat storage means is configured to be irremovable from the receiving space, a ratio of the first volume of the receiving space to the second volume of the phase change material is between 2:1 and 7:1, an entire outer surface of the housing of the latent heat storage means that surrounds the phase change material is in direct contact with the water during usage.

18. The method according to claim 17, wherein the latent heat storage means is placed loosely in the receiving space.

19. The method according to claim 17, wherein the phase change material is solid at 20° C.

20. A method for manufacturing a hot water bottle configured to be brought in at least indirect contact with a living being, comprising:

preparing two blank plates for forming a receiving space having a first volume, at least one of the two blank plates being configured to at least partially form a flexible outer wall of the hot water bottle, wherein a filling and emptying opening in fluid communication with the receiving space is formed, wherein the filling and emptying opening has a thread for attaching a closure that closes and seals the filling and emptying opening, placing at least one latent heat storage means between the two blank plates, the latent heat storage means comprising:

a housing formed as a flexible film composed of a polymer material and defining a plurality of fluidly connected chambers, and a second volume of phase change material disposed in the plurality of fluidly connected chambers of the housing, the phase change material comprising sodium acetate trihydrate and having a property of absorbing energy during an endothermic phase transition when warmed by water and releasing energy in the form of heat during an exothermic phase transition when the temperature of the water falls below a phase transition temperature of the phase change material, wherein all sides of the latent heat storage means are in contact with the water during usage, connecting the two blank plates to each other with the at least one latent heat storage means disposed loosely between two blank plates, wherein: the latent heat storage means is configured to be irremovable from the receiving space, a ratio of the first volume of the receiving space to the second volume of the phase change material is between 2:1 and 7:1, and an entire outer surface of the housing of the latent heat storage means that surrounds the phase change material is in direct contact with the water during usage.

21. The method according to claim 20, wherein the phase change material is solid at 20° C.

\* \* \* \* \*